(12) United States Patent
Belkovi et al.

(10) Patent No.: US 10,413,491 B2
(45) Date of Patent: Sep. 17, 2019

(54) IN VIVO ACCELERATED DEGRADATION OF POLYSACCHARIDE-CONTAINING FILLERS

(71) Applicant: MERZ PHARMA GMBH & CO. KGAA, Frankfurt am Main (DE)

(72) Inventors: Lubin Belkovi, Friedrichsdorf (DE); Franck Villain, Paris (FR); Andreas Krause, Frankfurt am Main (DE); Colin Drabe, Mainz (DE)

(73) Assignee: MERZ PHARMA GMBH & CO. KGAA, Frankfurt am Main (DE)

( * ) Notice: Subject to any disclaimer, the term of this patent is extended or adjusted under 35 U.S.C. 154(b) by 0 days.

(21) Appl. No.: 15/300,264

(22) PCT Filed: Apr. 1, 2015

(86) PCT No.: PCT/EP2015/000711
§ 371 (c)(1),
(2) Date: Sep. 28, 2016

(87) PCT Pub. No.: WO2015/149946
PCT Pub. Date: Oct. 8, 2015

(65) Prior Publication Data
US 2017/0172865 A1    Jun. 22, 2017

(30) Foreign Application Priority Data
Apr. 2, 2014   (EP) .................................... 14001218

(51) Int. Cl.
| | |
|---|---|
| *A61K 31/375* | (2006.01) |
| *A61K 8/22* | (2006.01) |
| *A61K 31/729* | (2006.01) |
| *A61K 33/40* | (2006.01) |
| *A61Q 90/00* | (2009.01) |
| *A61K 31/738* | (2006.01) |
| *A61K 8/42* | (2006.01) |
| *A61K 8/67* | (2006.01) |
| *A61Q 19/08* | (2006.01) |
| *A61K 45/06* | (2006.01) |
| *A61K 31/07* | (2006.01) |
| *A61K 31/167* | (2006.01) |
| *A61K 31/355* | (2006.01) |
| *A61K 33/20* | (2006.01) |
| *A61K 33/24* | (2019.01) |
| *A61K 33/26* | (2006.01) |
| *A61K 33/34* | (2006.01) |
| *A61K 31/122* | (2006.01) |
| *A61K 33/18* | (2006.01) |
| *A61K 33/30* | (2006.01) |

(52) U.S. Cl.
CPC .............. *A61K 8/22* (2013.01); *A61K 8/42* (2013.01); *A61K 8/676* (2013.01); *A61K 31/07* (2013.01); *A61K 31/122* (2013.01); *A61K 31/167* (2013.01); *A61K 31/355* (2013.01); *A61K 31/375* (2013.01); *A61K 31/738* (2013.01); *A61K 33/18* (2013.01); *A61K 33/20* (2013.01); *A61K 33/24* (2013.01); *A61K 33/26* (2013.01); *A61K 33/30* (2013.01); *A61K 33/34* (2013.01); *A61K 33/40* (2013.01); *A61K 45/06* (2013.01); *A61Q 19/08* (2013.01); *A61Q 90/00* (2013.01); *A61K 2800/91* (2013.01)

(58) Field of Classification Search
None
See application file for complete search history.

(56) References Cited

U.S. PATENT DOCUMENTS

| | | | |
|---|---|---|---|
| 4,226,851 A | 10/1980 | Sompayrac | |
| 2006/0246033 A1* | 11/2006 | Ninan | A61K 9/0019 424/85.5 |
| 2010/0136070 A1* | 6/2010 | Dobak | A61K 8/24 424/401 |
| 2012/0148667 A1 | 6/2012 | Callegaro et al. | |
| 2013/0244970 A1* | 9/2013 | Lebreton | A61K 8/42 514/54 |

FOREIGN PATENT DOCUMENTS

| | | |
|---|---|---|
| GB | 2285218 A | 7/1995 |
| GB | 2471253 A | 12/2010 |

OTHER PUBLICATIONS

Brody, Dermatol Surg, 2005, 31, 893-897.*
Toluene Solvent Properties. Obtained online at: http://macro.lsu.edu/howto/solvents/toluene.htm. Downloaded on Dec. 1, 2017.*
Q3C-Tables and List Guidance for Industry, U.S. Department of Health and Human Services, Food and Drug Administration, Jun. 20117, obtained online at: https://www.fda.gov/downloads/Drugs/GuidanceComplianceRegulator, pp. 1-8.*
Voschin et al., J Ann Acad Dermatol, AB189. (Year: 2009).*
International Search Report and Written Opinion of International Patent Application No. PCT/EP2015/000711 dated Jul. 15, 2015.
Robertson W.V. et al., "The Degradation of Mucins and Polysaccharides by Ascorbic Acid and Hydrogen Peroxide", The Biochemical Journal, Sep. 1941, pp. 903-908, vol. 35, No. 8-9.

(Continued)

*Primary Examiner* — Abigail Vanhorn
(74) *Attorney, Agent, or Firm* — McBee Moore Woodward & Vanik IP, LLC

(57) ABSTRACT

The present invention relates to a composition for the in vivo degradation of polysaccharide-containing fillers by radical degradation. The composition of the invention comprising at least one source of oxygen free radicals and at least one catalyst of oxygen free radical generation from the at least one source of oxygen free radicals. The present invention further relates to methods and uses of said composition for filler correction or reversal.

17 Claims, 4 Drawing Sheets

(56) References Cited

OTHER PUBLICATIONS

Smidsroed et al., "Degradation of Alginate in the Presence of Reducing Compounds", Acta Chemica Scandinavica, Jan. 1, 1963, pp. 2628-2637, vol. 17, No. 10, Munksgaard, Copenhagen, DK.

Skanse, Bengt et al., "Oxidatire Breakdown of Hyaluronic and Chondroitin Sulphuric Acid", Acta Physiologica Scandinavica, Sep. 1, 1943, pp. 37-51, vol. 6, No. 1.

Cohen, Joel L., "Understanding, Avoiding, and Managing Dermal Filler Complications", Dermatologic Surger, Jun. 1, 2008, vol. 34, No. S1.

Soltes, L., et al., "Degradation of high-molar-mass hyaluronan by an oxidative system comprising ascorbate, Cu (II), and hydrogen peroxide: Inhibitory action of antiinflammatory drugs—Naproxen and acetylsalicyclic acid," Journal of Pharmaceutical and Biomedical Analysis, (2007), vol. 44: 1056-1063.

* cited by examiner

IN VIVO ACCELERATED DEGRADATION OF POLYSACCHARIDE-CONTAINING FILLERS

CROSS-REFERENCE TO RELATED APPLICATIONS

This application is a National Stage entry of International Application No. PCT/EP2015/000711, filed Apr. 1, 2015, which claims priority to European Patent Application No. 14001218.8, filed Apr. 2, 2014. The disclosures of the priority applications are incorporated in their entirety herein by reference.

FIELD OF THE INVENTION

The present invention relates to a composition for the in vivo degradation of polysaccharide-containing fillers by radical degradation. The present invention further relates to methods and uses of said composition for filler correction or reversal.

BACKGROUND OF THE INVENTION

Non-surgical aesthetic treatments are becoming increasingly popular because they are quicker, less painful and more subtle than plastic surgery. Injection of dermal fillers is one of the most commonly performed aesthetic procedures and is used for wrinkle treatment, lip enhancement, cheek augmentation and scar removal. However, in some case, serious complications can occur such as misplacement of the filler, overcorrection of areas such as the nose, or the formation of nodules. In case of the most widely used hyaluronic acid (HA) fillers, hyaluronidase can be used to enzymatically decompose and eliminate the hyaluronic acid polymers that cause the complications.

The use of hyaluronidase has, however, several drawbacks. First, it is not approved for filler correction or reversal (off-label use). In fact, its use is even banned in some countries. Furthermore, because of its animal origin, hyaluronidase has been shown to cause allergic reactions and cases of severe angioedema have been described. In addition, the enzymatic degradation of fillers, especially in case of high volumizing fillers that are typically highly crosslinked, is often not fast enough for optimum convenience and control. Moreover, fillers based on polysaccharides other than HA, such as Radiesse® (CMC) or Novabel® (alginate), cannot be degraded using hyaluronidase.

OBJECT OF THE INVENTION

In view of the above, the object of the present invention is the provision of compositions and methods to efficiently and rapidly degrade various polysaccharide fillers in a simple and safe manner.

SUMMARY OF THE INVENTION

The above object is solved by the provision of a composition for the in vivo degradation of polysaccharide-containing fillers (or "filler-degrading composition"), comprising at least one source of oxygen free radicals and at least one catalyst of oxygen free radical generation from the at least one source of oxygen free radicals.

In a further aspect, there is provided a composition according to the present invention for use in the treatment of unwanted polysaccharide-containing filler depots or polysaccharide-containing filler misplacements, asymmetries, and overcorrections.

In another aspect, the present invention relates to the use of the composition according to the present invention for the in vivo degradation of polysaccharide-containing fillers for therapeutic or cosmetic purposes.

In yet another aspect, the present invention provides a kit, comprising (a) at least one source of oxygen free radicals as defined herein, and (b) at least one catalyst of oxygen free radical generation from the at least one source of oxygen free radicals as defined herein, wherein components (a) and (b) are provided separately and independently of one another in solid or liquid form, or wherein components (a) and (b) are provided in combination in the form of a mixture of solids or in the form of a solution.

In a still further aspect, the present invention provides a pharmaceutical composition, comprising (a) at least one source of oxygen free radicals as defined herein, (b) at least one catalyst of oxygen free radical generation from the at least one source of oxygen free radicals as defined herein, and (c) a pharmaceutically acceptable carrier.

In a yet further aspect, the present invention provides a method for the in vivo degradation of polysaccharide-containing fillers, comprising administering to a subject a filler-degrading composition or a pharmaceutical composition according to the present invention into said filler or in the close proximity of said filler.

Preferred embodiments of the present invention are set forth in the appended dependent claims.

DETAILED DESCRIPTION OF THE INVENTION

Figure 1:
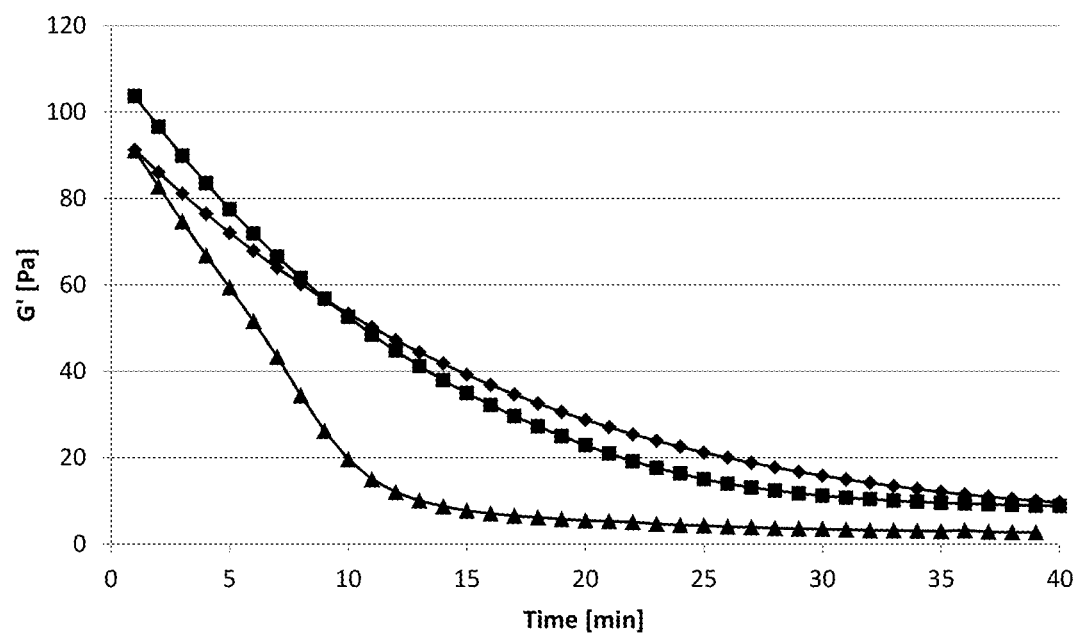
FIG. 1 illustrates the influence of varying $H_2O_2$ concentrations on the degradation of a HA gel. The decrease in storage modulus G' over time is shown for a crosslinked HA gel at 24 mg/ml made from the crosslinked HA matrix used in the manufacturing of Glytone 3 (Merz Aesthetics) for 0.11 mmol (3.91 mg) $H_2O_2$+0.005 mmol (1.01 mg) ascorbic acid (AA) (♦), 0.15 mmol (5.08 mg) $H_2O_2$+0.007 mmol (1.3 mg) AA (■), and 0.23 mmol (7.83 mg) $H_2O_2$+0.011 mmol (2.02 mg) AA (▲).

The inventors of the present invention have surprisingly found that a composition, comprising at least one source of oxygen free radicals and at least one catalyst of oxygen free radical generation from said at least one source of oxygen free radicals (in the following also referred to as "filler-degrading composition"), is capable of efficiently and rapidly degrading polysaccharide-containing fillers in a safe and reliable manner. Furthermore, polysaccharide-containing fillers can be degraded in a controlled manner. In particular, it was found that polysaccharide-containing fillers can be decomposed within minutes, i.e. faster than or at least as fast as the conventional treatment using hyaluronidase. Also, since the polysaccharides are decomposed by radical degradation, even highly crosslinked fillers that are less prone to degradation by hyaluronidase, can be rapidly and reliably decomposed.

Moreover, the filler-degrading composition of the present invention not only rapidly degrades HA fillers (e.g., Belotero®, Glytone®, Restylane®, Prevelle®, Juvéderm®, and Téosyal®), but also other fillers such as CMC fillers (e.g., Radiesse®, a Ca-hydroxyapatite containing carboxymethyl cellulose (CMC)-based filler) or alginate-based fillers (e.g., Novabel®). Further, only minute amounts of the filler-degrading composition are needed to allow the network of a particular filler to be degraded, leading to rapid elimination of the filler components.

Another advantage is that the risk of adverse effects associated with conventional hyaluronidase treatment, for example allergic reactions and xenogeneic induced inflammation, is minimized. Furthermore, the filler-degrading composition of the present invention can easily be prepared sterile and the substances required for its preparation are cheap and stable.

In a first aspect the present invention relates to a composition for the in vivo degradation of polysaccharide-containing fillers, comprising at least one source of oxygen free radicals and at least one catalyst of oxygen free radical generation from the at least one source of oxygen free radicals.

Within the present invention, the term "polysaccharide-containing filler(s)" is not particularly limited and includes any polysaccharide-based fillers, including fillers based on hyaluronic acid (HA), carboxymethyl cellulose (CMC) and alginate. The term "filler", either used alone or in the context of an expression such as "polysaccharide-containing filler", is not intended to imply any restrictions and includes any material for replacing a biological tissue, filling a biological tissue, or augmenting/increasing the volume of a biological tissue.

For example, the filler may be a filler used in rheumatology (e.g., as a replacement agent of the synovial fluid), in urology/gynecology (e.g., as an agent for increasing the volume of the sphincter or the urethra), in ophthalmology (e.g., as an adjuvant in cataract surgery or for glaucoma treatment), in surgery (e.g., for increasing the volume of the vocal cords), and in dermato-cosmetics (e.g., for wrinkle treatments). Within the context of the present invention, the filler is preferably a dermal filler, i.e. a filler used in the (dermo)cosmetic field, such as for augmenting or filling of wrinkles or fine lines of the skin (e.g., nasolabial folds, marionette lines, chin folds, lower jawlines, oral commissure, and the like), filling cutaneous depressions, masking scars, increasing the volume of the lips, augmenting cheeks, correcting facial parts like the nose, and/or improving skin hydration and skin texture.

As used herein, the term "source of oxygen free radicals" means any compound capable of resulting in the generation of oxygen free radicals. Within the context of the present invention, the generation of oxygen free radicals generally takes place upon contacting the polysaccharide-containing filler that is to be degraded with the filler-degrading composition of the present invention under appropriate processing conditions, in particular under in vivo conditions (i.e. the conditions prevailing at the administration site of the composition in the human body, such as a temperature of about 35° C. (skin temperature)).

The term "oxygen free radical", as used herein means a free radical of an oxygen atom or an oxygen compound. A "free radical" is generally defined as an atom or molecule with one or more unpaired electrons. The unpaired electron alters the chemical reactivity of the molecule/atom, making it more reactive than the corresponding non-radical form. Thus, an "oxygen free radical" within the meaning of the present invention refers to a free radical in which an unpaired electron is on an oxygen atom. Exemplary oxygen free radicals generated from the source of oxygen free radicals include, but are not limited to, one or more of the superoxide anion radical ($O_2^{\cdot-}$), the hydroxyl radical ($\cdot OH$), and the perhydroxyl radical ($HO_2\cdot$).

Within the context of the present invention, the source of oxygen free radicals may be a peroxide, a perchlorate (e.g., potassium or sodium perchlorate), a hypochlorite (e.g., sodium hypochlorite), or a compound containing a hypervalent iodine. Particularly suitable for use herein are peroxides. The term "peroxide", as used herein, generally refers to a compound containing an oxygen-oxygen single bond (i.e., a O—O group or "peroxo" group) or to the peroxide anion ($O_2^{2-}$). The peroxide for use herein may by an organic peroxide or an inorganic peroxide.

Exemplary organic peroxides for use in the present invention include, but are not limited to, organic peroxide compounds of general structure ROOR', organic hydroperoxides of general structure ROOH and salts thereof, organic peroxy acids of general structure RC(O)OH and salts thereof, and peresters of general structure RC(O)OOR', wherein R and R' are each independently an organic moiety that is not particularly limited, but may be an organic group of 1 to 30 (e.g., 1 to 10) carbon atoms and 0 to 5 (e.g., 0, 1 or 2) heteroatoms selected from N, O and S. Preferably, R and R' are each independently a linear or branched $C_1$-$C_{20}$ (e.g., $C_1$-$C_{10}$ or $C_1$, $C_2$, $C_3$, $C_4$, $C_5$ or $C_6$) alkyl group, a $C_6$ aryl group, or a $C_7$-$C_{22}$ aralkyl group, each of which may be optionally substituted (e.g., by halogen, OH or $NH_2$). Specific examples of suitable organic peroxide are, but not limited to, t-butyl hydrogenperoxide, cumene hydroperoxide, dicumyl peroxide, dibenzoylperoxide, meta-Chloroperoxybenzoic acid (mCPBA), and peracetic acid or salts thereof.

Suitable inorganic peroxides include hydrogen peroxide ($H_2O_2$) and its adducts, peroxides of alkali metals, alkaline earth metals and transition metals, persulfates (e.g., salts of peroxomonosulfate or peroxydisulfate), and percarbonates (e.g. sodium percarbonate). Preferred for use herein are peroxides of alkali metals (e.g. lithium peroxide, sodium peroxide, potassium peroxide), peroxides of alkaline earth metals (e.g., magnesium peroxide, calcium peroxide, strontium peroxide, and barium peroxide), peroxides of transition metals (e.g., zinc peroxide, nickel peroxide), and hydrogen peroxide ($H_2O_2$). Most preferred is hydrogen peroxide and adducts thereof (e.g. hydrogen peroxide-urea).

In accordance with the present invention, the filler-degrading composition further includes a catalyst of oxygen free radical generation. Within the context of the present invention, the term "catalyst of oxygen free radical generation" means any compound that functions as a catalyst in the generation of free oxygen radicals from the at least one source of oxygen free radicals (e.g., hydrogen peroxide). In other words, a "catalyst of oxygen free radical generation" is intended to mean any compound that is capable of promoting (enhancing) oxygen free radical generation, especially increasing the rate of oxygen free radical generation, from the source of oxygen free radicals. The term "catalyst", as used herein, is to be broadly construed to include, inter alia, compounds that are consumed during oxygen free radical generation. Thus, the term "catalyst" may herein also interchangeably used with the term "oxygen radical promoter" or the term "booster".

As examples of suitable catalysts of oxygen free radical generation from the at least one source of oxygen free radicals, there can be mentioned transition metals, e.g. Fe(III), Cu(II), Cr(II), V(II), Ti(III), Co(II)), and salts thereof, and natural antioxidants, e.g. vitamins such as vitamin A (including retinol, retinal, retinoic acid, and provitamin A carotenoids such as beta carotene), vitamin C and vitamin E (including tocopherols and tocotrienols), glutathione, ubiquinone (Coenzyme Q10), and phenols and polyphenols (e.g. flavonoids, isoflavonoids, and anthocyanines), wherein vitamin C is a preferred natural antioxidant. Preferred for use herein are transition metals and salts thereof and, in particular, ascorbic acid (vitamin C) and salts and/or derivatives thereof. Suitable ascorbic acid derivatives include esters of ascorbic acid. Exemplary derivatives are sodium ascorbyl phosphate and ascorbyl tetraisopalmitate.

Furthermore, the molar ratio of the oxygen free radical source (e.g., hydrogen peroxide or an adduct thereof) to the catalyst (e.g., ascorbic acid or a derivative thereof) may be, for example, in the range of between about 100:1 to 2:1, preferably in the range of about 50:1 to 10:1 or 20:1 to 5:1. If used in liquid form, the concentration of the oxygen free radical source (e.g., hydrogen peroxide or an adduct thereof) may be in the range of about 0.1 M to 10.0 M or 1.0 M to 10.0 M, and the concentration of the catalyst (e.g., ascorbic acid or a derivative thereof) may be in the range of about 0.01 M to 1.0 M or 0.1 M to 1.0 M.

Preferably, the composition of the present invention comprises hydrogen peroxide or a derivate (e.g., an adduct) thereof, such as hydrogen peroxide-urea (acting as a source, particularly sole source, of oxygen free radicals), and ascorbic acid or a derivative thereof, such as ascorbic acid esters (acting as a "booster", particularly sole booster). The concentration of hydrogen peroxide or derivative thereof in the composition is preferably between 15 mM (0.05% w/v) and 2.9 M (10% w/v), more preferably between 29 mM (0.1% w/v) and 1.45 M (5% w/v), and most preferably between 0.29 M (1% w/v) and 0.88 M (3% w/v) (the percentages in brackets refer to hydrogen peroxide only). The concentration of ascorbic acid or derivative thereof in the composition is preferably between 5.7 mM (1 mg/ml) and 2.8 M (500 mg/ml), preferably between 28.3 mM (5 mg/ml) and 0.57 M (100 mg/ml), particularly preferred between 57 mM (10 mg/ml) and 0.28 M (50 mg/ml), and most preferable between 0.085 M (15 mg/ml) and 0.17 M (30 mg/ml) (the mg/ml concentration values in brackets refer to ascorbic acid only).

The composition of the present invention may further include additional substances like buffers (e.g., phosphate buffer), osmolarity adjusting agents, antioxidants, salts, chelating agents, peptides, proteins, polysaccharides, active ingredients (e.g., pharmaceutically active ingredients), and the like. In a preferred embodiment, the composition of the present invention further comprises an anesthetic agent. The anesthetic agent is preferably a local anesthetic compound, in particular a "caine-type" compound, such as lidocaine, tetracaine, benzocaine, procaine, cocaine, mepivacaine and bupivacaine, and is most preferably lidocaine.

According to a preferred embodiment of the present invention, the filler-degrading composition is further characterized by having the ability to degrade a crosslinked HA gel (e.g., Belotero® Intense) within less than 20 minutes after mixing of 40 µl of the composition in form of an aqueous solution with 1000 mg of said crosslinked HA gel, wherein said degradation is indicated by a decline in the storage modules (G') of more than 90% of the start value of the mixture of said aqueous solution and said crosslinked HA gel.

The form of the filler-degrading composition is not particularly limited and the composition, for example, may be a liquid (e.g., an aqueous solution, preferably a physiological solution), a semi-solid (e.g., a gel or paste), or a solid (e.g., a powder or a dry salt). Further, the filler degrading composition is generally sterile and can be advantageously sterilized in an easy manner by, for example, steam sterilization, gamma irradiation or sterile filtration.

In a further aspect, the present invention relates to a filler-degrading composition as described herein for use in the treatment of, typically unwanted, polysaccharide-containing filler depots or of polysaccharide-containing filler misplacements, asymmetries and overcorrections.

The use generally involves administration of an effective amount of the filler-degrading composition by injection into or in the close proximity of the filler. This is, for administration by injection, the filler-degrading composition is necessarily present in injectable form such as in liquid form. Suitable needle sizes can be selected according to location and size or volume of the filler mass to be removed. A 30-gauge needle may be used for more superficial nodules and a 27-gauge or 26-gauge needle for deeper nodules. The composition may be injected intradermally or subcutaneously using an appropriate injection technique such as the serial puncture technique. In case of superficial filler masses, the injection is preferably made just beneath the filler mass.

As used herein, the term "effective amount" refers to the amount of a compound sufficient to achieve desired therapeutic or cosmetic results. A therapeutically or cosmetically effective amount can be administered in one or more administrations, applications or dosages and is not intended to be limited to a particular administration regimen.

The "treatment" may be a cosmetic or a therapeutic treatment. A cosmetic treatment is targeted to a filler implanted for cosmetic purposes (e.g., for wrinkle reduction). A therapeutic treatment is targeted to a filler implanted for therapeutic purposes (e.g., for increasing the volume of the sphincter, urethra or vocal cords). Typically, the "treatment" is a degradation, decomposition, reduction, elimination or removal of unwanted polysaccharide-containing filler depots or of polysaccharide-containing filler misplacements, asymmetries and overcorrections.

Within the context of the present invention, the term "polysaccharide-containing filler depots" broadly refers to any implanted depot of a polysaccharide-containing filler. The term "depot", as used herein, is intended to mean implanted filler materials or masses such as HA gels injected into soft tissues. Usually, the polysaccharide-containing filler depots are "unwanted", i.e. polysaccharide-containing filler depots causing patient discomfort and which often, independently of the subjective perception of the subject, present as unsightly or unaesthetic lumps or masses. The term "misplacements", as used herein, typically refers to fillers that are not injected at the right place, resulting in unwanted contours and/or volume increases at undesired places. The term "asymmetries", as used herein, usually refers to the fact that irregularities (asymmetries) may present after filler application (injection). In particular, contour asymmetries of the face may occur that need correction or adjustment. The term "overcorrections", as used herein, generally means excess filler use resulting in an undesirably high volume increase, which often leads to unaesthetic, soft, protruding masses under the skin.

The amounts of the oxygen free radical source and of the catalyst of oxygen free radical generation required for the degradation and elimination of the polysaccharide-containing filler is not particularly limited, and may be appropriately selected by those skilled in the art using common technical knowledge and routine work. Generally, about 0.005 mmol to 50.0 mmol, preferably 0.01 mmol to 10 mmol or 0.05 mmol to 2.0 mmol or 0.1 mmol to 1.0 mmol or 0.1 mmol to 0.5 mmol of said oxygen free radical source and about 0.0005 mmol to 2.8 mmol, preferably about 0.001 mmol to 1.0 mmol or 0.005 to 0.5 mmol or 0.01 to 0.05 mmol of said catalyst may be used for degrading 1.0 g of a polysaccharide-containing filler.

In another aspect, the present invention relates to the use of a composition according to the present invention for the in vivo degradation of polysaccharide-containing fillers for therapeutic or cosmetic purposes. With regard to this aspect, the explanations set out above in relation to the use of the filler-degrading composition of the present invention equally apply.

The term "degradation" within the meaning of the present invention generally refers to a process which results in the degradation, decomposition, rupture and/or destruction of the gel network of the filler, thereby leading to solvation by the aqueous solution in the tissue or by the (buffer) solution of the injected product. The degradation can be monitored by measuring the decrease in storage modulus G' over time which is an indicator of mechanical integrity/mechanical strength.

In yet another aspect, the present invention relates to a kit, comprising (a) at least one source of oxygen free radicals as defined herein, and (b) at least one catalyst of oxygen free radical generation from the at least one source of oxygen free radicals as defined herein, wherein components (a) and (b) are provided separately and independently of one another in solid or liquid form, or wherein components (a) and (b) are provided in combination in the form of a mixture of solids or in the form of a solution.

The kit may, for example, comprise containers (e.g., vials) pre-filled with the at least one source of oxygen free radicals and the catalyst, either separately or in combination with each other, or in combination with other substances (e.g., the optionally present additional compounds mentioned above), and with or without a local anesthetic such as lidocaine. In addition, the kit may comprise a solution (e.g., water, a buffer solution, a physiological saline) for preparing an injectable filler-degrading composition and, optionally, one or more syringes for injection. The kit is preferably intended for use in the treatment of misplacements, asymmetries and overcorrections of polysaccharide-containing dermal fillers.

It therefore may also contain instructions for use in the treatment of misplacements, asymmetries and overcorrections of polysaccharide-containing dermal fillers.

In a still further aspect, the present invention relates to a pharmaceutical composition, comprising (a) at least one source of oxygen free radicals as defined herein, (b) at least one catalyst of oxygen free radical generation from the at least one source of oxygen free radicals as defined herein, and (c) a pharmaceutically acceptable carrier.

As used herein, the term "pharmaceutically acceptable" refers to those compounds or substances which are, within the scope of sound medical judgment, suitable for contact with the tissues of mammals, especially humans, without excessive toxicity, irritation, allergic response and other problem complications. The term "carrier", as used herein, relates to a diluent, solvent, excipient or vehicle whereby the active ingredient is administered. Pharmaceutically acceptable carriers for use herein can be, for example, sterile liquids, dispersions, or gels. Preferred carriers are those suited for subcutaneous or intradermal injection, for example a physiological phosphate buffer like PBS (phosphate buffered saline) at, e.g., a pH of 6.8 to 7.5.

The pharmaceutical composition generally includes an effective amount of the at least one source of oxygen free radicals and the at least one catalyst of oxygen free radical generation. The pharmaceutically acceptable composition according to the present invention is typically administered by injection to hasten the degradation process and eliminate the filler in order to restore the tissue or skin to its previous state.

Furthermore, the pharmaceutical composition, like the filler-degrading composition of the present invention, may include one or more additional pharmaceutically acceptable substances that are co-administered, for example pharmaceutical acceptable excipients such as vitamins or anesthetic agents. Suitable anesthetic agents include local anesthetics such as lidocaine.

In a yet further aspect, the present invention relates to a method for the in vivo degradation of polysaccharide-containing fillers, comprising administering to a subject a composition according to the present invention or a pharmaceutical composition according to the present invention into said filler or in the close proximity of said filler.

The filler-degrading composition and pharmaceutical composition according to the present invention are administered in an effective amount to obtain the desired result, i.e. the degradation, decomposition, reduction, removal or elimination of the polysaccharide-containing filler of the treated subject. The composition may be conveniently administered by injection. In case of dermal fillers, the composition is generally applied by subcutaneous or intradermal injections, for example using the serial puncture technique.

The present invention will now be further illustrated by the following, non-limiting examples.

EXAMPLES

The examples provided below demonstrate that the composition according to the present invention ("filler-degrading composition), comprising at least one source of oxygen free radicals and at least one catalyst of oxygen free radical generation (the catalyst is also referred to as "booster" in the following), is capable of efficiently degrading different non-commercial and commercial dermal filler gels in a safe, simple and reliable way. Thus, the filler-degrading compositions according to the present invention meet the long-sought need in the art for an efficient method for the in vivo degradation and elimination of resorbable fillers, in particular of crosslinked biopolymer fillers, in order to correct misplacements, asymmetries, overcorrections, and the like.

Materials and Methods

All filler-degrading solutions ($H_2O_2$ and Urea*$H_2O_2$ (radical sources) with or without ascorbic acid (booster)) were freshly prepared daily shortly prior to use in order to avoid a loss in their degradation potency (e.g., due to the light sensitivity of ascorbic acid in aqueous solution). The 30% (v/v) aqueous $H_2O_2$ stock solution and the Urea*$H_2O_2$ stock reagent used were stored in the dark under cooled conditions prior to use, whereas no particular storage restrictions apply to the other reagents used. In all experiments, distilled water was used for dilution purposes.

The degradation process was monitored by measuring different rheological properties, i.e. the storage modulus G' [Pa], the complex viscosity η [Pa·s] and the tan δ (the ratio G"/G'), over time. The measurements were carried out using an MCR 302 Anton Paar rheometer (50 mm diameter, cone 1°) at a temperature of 25° C.

Degradation Study Using Pure 30% Aqueous $H_2O_2$:

In this study (also referred to as "slow degradation" study), 500 µl of gel were decomposed by addition of 500 µl of a pure 30% aqueous $H_2O_2$ solution. More specifically, 500 µl of gel were filled into a first syringe connected to a second syringe via a luer lock adapter. Next, 500 µl of a 30% aqueous $H_2O_2$ solution was added into the second syringe. The gel and the $H_2O_2$ solution were then homogenized by pushing both plungers 50 times back and forth. Next, the homogenized mixture was placed on a rheometer plate for measurement.

Degradation Study Using 0.23 mmol (7.83 mg) $H_2O_2$+ 0.011 mmol (2.02 mg) AA:

In this study (also referred to as "fast degradation" study), 1000 µl of gel were decomposed by addition of 40 µl of a mixture of aqueous $H_2O_2$ and ascorbic acid (AA). First, 7.987 ml of 30% aqueous $H_2O_2$ were diluted by addition of 2.013 ml water. In a separate tube, 676 mg ascorbic acid was dissolved in 3.33 ml of water. 10 µL of the ascorbic acid solution and 30 µL of the diluted $H_2O_2$ solution were then mixed in a separate vessel. Next, 1000 µl of the gel were filled into a first syringe connected to a second syringe via a luer lock adapter. The $H_2O_2$/ascorbic acid solution was then added into the second syringe. Subsequently, the gel and the $H_2O_2$/ascorbic acid solution were homogenized by pushing both plungers 50 times back and forth. Finally, the homogenized mixture gel was placed on the rheometer plate for measurement.

Degradation Study Using 0.31 mmol (28.9 mg) Urea*$H_2O_2$+0.04 mmol (8.2 mg) AA:

In this study (also referred to as "alternative fast degradation" study), 1000 µl of gel were decomposed by addition of 40 µl of a mixture of Urea*$H_2O_2$ and ascorbic acid (AA). First, 722 mg of Urea*$H_2O_2$ and 205 mg of ascorbic acid were weighted in the same vessel. 1000 µl of distilled water was added, followed by gentle mixing. Next, 1000 µl of gel were filled into a first syringe connected to a second syringe via a luer lock adapter. The Urea*$H_2O_2$/ascorbic acid solution was added into the second syringe. The gel and the Urea*$H_2O_2$/ascorbic acid solution were then homogenized by pushing both plungers 50 times back and forth. Finally, the homogenized mixture was placed on the rheometer plate for measurement.

Example 1

Degradation Capacity of a Mixture of $H_2O_2$+Ascorbic Acid Versus Pure 30% $H_2O_2$ A medium crosslinked HA gel, i.e. the crosslinked HA matrix used for manufacturing Glytone 3 (Merz Aesthetics), concentrated at 24 mg/ml and sterilized at 127° C. for 4 minutes, was decomposed using 0.23 mmol $H_2O_2$+5 mol % (0.011 mmol) AA and, as a comparison, pure 30% aqueous $H_2O_2$. The degrading solution was prepared as described above. The storage modulus G' as an indicator of mechanical integrity was measured over time (see Table 1).

TABLE 1

Degradation using $H_2O_2$ + AA versus pure 30% $H_2O_2$

| Filler-degrading composition | G' at t = 0 min | G' after 20 min | Delta |
|---|---|---|---|
| 30% aq. $H_2O_2$ | 96 Pa | 70 Pa | −28% |
| 0.23 mmol $H_2O_2$ + 5 mol % (0.011 mmol) AA | 106 Pa | 6 Pa | −95% |

As can be seen from Table 1, the inventive mixture of $H_2O_2$+AA leads to an unexpected dramatic increase in the degradation rate compared to the slow degradation by pure 30% $H_2O_2$. This is all the more surprising, when keeping in mind that in case of the $H_2O_2$+AA degradation solution a volume of only 40 µL was used for decomposition of 1000 mg gel, whereas in case of the pure 30% $H_2O_2$ solution a volume of no less than 500 µl was used for decomposition of 500 mg gel.

Example 2

Influence of Varying $H_2O_2$ Concentrations on the Degradation Process

The same medium crosslinked gel as in Example 1 was decomposed using varying concentrations of $H_2O_2$ while maintaining AA constant at 5 mol %. The respective degradation solutions were prepared as described above under "Materials and Methods", wherein the 30% $H_2O_2$ stock solution was appropriately diluted with distilled water to obtain various $H_2O_2$ concentrations. The results of the rheological measurements are shown in Table 2.

TABLE 2

Various amounts of $H_2O_2$ mixed with 5 mol % AA

| Filler-degrading composition | G' at t = 0 min* | G' after 20 min | Delta |
|---|---|---|---|
| 0.03 mmol $H_2O_2$ + 0.0015 mmol AA | 124 Pa | 67 Pa | −46% |
| 0.06 mmol $H_2O_2$ + 0.003 mmol AA | 115 Pa | 59 Pa | −49% |
| 0.11 mmol $H_2O_2$ + 0.005 mmol AA | 91 Pa | 28 Pa | −70% |
| 0.15 mmol $H_2O_2$ + 0.007 mmol AA | 103 Pa | 21 Pa | −80% |
| 0.23 mmol $H_2O_2$ + 0.011 mmol AA | 93 Pa | 5 Pa | −95% |

*The varying start values are a result of the differences in gel processing times As is evident from Table 2, the degradation rate increases with increasing $H_2O_2$ concentrations. The use of increasing $H_2O_2$ concentrations of higher than 7.68 mM caused only incremental increases of the degradation rate (results not shown).

Moreover, as can be seen from FIG. 1, the mixture of 0.23 mmol $H_2O_2$ and 0.011 mmol AA (indicated by black triangles in FIG. 1) is particularly advantageous for use herein because (a) it degrades the gel very quickly, (b) the degradation follows a linear relationship with time as indicated by the linear slope of the plot of storage modulus G' versus time (t=0-10 min) shown in FIG. 1, and (c) it leads to full degradation of the gel (see FIG. 1, G' is less than about 15 Pa after 10 min).

Example 3

Influence of Varying AA Concentrations on the Degradation Process

The same medium crosslinked gel as in Example 1 was decomposed using different concentrations of AA (2.5 mol % or 5 mol %) while maintaining $H_2O_2$ constant at 0.23 mmol. The solution of 0.23 mmol $H_2O_2$+5 mol % AA (i.e. 0.011 mmol AA) was prepared as described above under "Materials and Methods", and the solution of 0.23 mmol $H_2O_2$+2.5 mol % (i.e. 0.005 mmol AA) was prepared in the same manner, except that half of the amount of AA was diluted in water. The results of the rheological measurements are shown in Table 3.

TABLE 3

Different mol % AA mixed with 0.23 mmol $H_2O_2$

| Filler-degrading composition | G' at t = 0 min | G' after 20 min | Delta |
|---|---|---|---|
| 2.5 mol % (0.005 mmol) AA + 0.23 mmol $H_2O_2$ | 117 Pa | 55 Pa | −53% |
| 5 mol % (0.011 mmol) AA + 0.23 mmol $H_2O_2$ | 89 Pa | 1.5 Pa | −98% |

From Table 3, it is seen that AA markedly accelerates gel degradation. It is believed that AA participates in and promotes free radical generation by $H_2O_2$, resulting in a greatly increased degradation rate. Thus, the data show that AA is a potent "booster" of free radical formation.

Example 4

Replacement of $H_2O_2$ by Urea*$H_2O_2$

In this example, the same medium crosslinked HA gel as in Example 1 was subjected to degradation by a solution of 0.31 mmol Urea*$H_2O_2$+13 mol % (0.04 mmol) AA. This solution was prepared as set out above under "Materials and Methods". For purposes of comparison, said gel was further subjected to degradation by a pure 30% $H_2O_2$ solution and a solution of 0.23 mmol $H_2O_2$+5 mol % (0.011 mmol) AA, which were both prepared in accordance with the methods described above under "Materials and Methods". The results of the rheology measurements are shown in Table 4.

TABLE 4

Degradation capacity of Urea * $H_2O_2$ with or without AA versus pure 30% $H_2O_2$

| Filler-degrading composition | G' at t = 0 min | G' after 20 min | Delta |
|---|---|---|---|
| Pure 30% $H_2O_2$ | 75 Pa | 54 Pa | −28% |
| 0.23 mmol $H_2O_2$ + 5 mol % (0.011 mmol) AA | 124 Pa | 11 Pa | −91% |
| 0.31 mmol Urea * $H_2O_2$ + 13 mol % (0.04 mmol) AA | 133 Pa | 53 Pa<br>11 Pa* | −60%<br>−92%* |

*After 30 min

As can be seen from Table 4, the solution of Urea*$H_2O_2$+13 mol % AA is able to efficiently degrade the medium crosslinked HA gel, although not as fast as the solution of $H_2O_2$+5 mol % AA (−91% vs. −60% after 20 min). However, after 30 min, the G' value for Urea*$H_2O_2$+13 mol % AA is about the same as that achieved for $H_2O_2$+5 mol % AA after 20 min (−91% vs. −92%). This is, the use of the Urea*$H_2O_2$ adduct in lieu of $H_2O_2$ also allows for a fast decomposition of the crosslinked HA gel.

In addition, the ability of the solution of Urea*$H_2O_2$+5 mol % AA to degrade different gels was confirmed in degradation studies using different gel formulations (results not shown; for $H_2O_2$+5 mol % AA see Example 5). Since the use of Urea*$H_2O_2$ allows for a much simpler product preparation (mixture of solids, i.e. solid Urea*$H_2O_2$ and solid AA), Urea*$H_2O_2$ is a preferred radical source for use within the present invention.

Example 5

Degradation of Various Fillers by a $H_2O_2$ and AA Containing Composition According to the Present Invention Different gel formulations were subjected to degradation using a solution of 0.23 mmol $H_2O_2$+5 mol % (0.011 mmol) AA prepared as described above under "Materials and Methods". The degradation process was monitored by measuring the storage modulus G' over time, and the results are shown in Table 5.

TABLE 5

Fast degradation of various gel formulations by a mixture of $H_2O_2$ and AA

| Gel formulations | Degrading composition | G' at t = 0 min | G' after a certain period of time value | at t = | Delta |
|---|---|---|---|---|---|
| Highly crosslinked HA gel (155 mg/ml, 9% BDDE) | $H_2O_2$/AA* | 515 Pa | 127 Pa<br>11 Pa | 10 min<br>20 min | −79%<br>−98% |
| Belotero ® Intense (Merz Aesthetics; double-crosslinked HA, 25.5 mg/ml) | $H_2O_2$/AA* | 53 Pa | 2 Pa | 5 min | −96% |
| Glytone ® 4 Original (Merz Aesthetics; commercial product, 24 mg/ml + 41 mg/ml mannitol) | $H_2O_2$/AA* | 44 Pa | 4 Pa | 7 min | −91% |
| CMC Gel (same CMC as in Radiesse ®; 29 mg/ml in water) | $H_2O_2$/AA* | 48 Pa | 3 Pa | 5 min | −94% |
| Radiesse ® (Merz Aesthetics) | $H_2O_2$/AA* | 392 Pa | 11 Pa | 6 min | −98% |

TABLE 5-continued

Fast degradation of various gel formulations by a mixture of $H_2O_2$ and AA

| Gel formulations | Degrading composition | G' at t = 0 min | G' after a certain period of time | | Delta |
| --- | --- | --- | --- | --- | --- |
| | | | value | at t = | |
| Novabel ® (Merz Pharmaceuticals; alginate, 15 mg/ml) | $H_2O_2$/AA* | 698 Pa | 140 Pa | 10 min | −80% |
| Gelatine Gel (Dr. Oetker; 0.5 g in 20 ml water) | $H_2O_2$/AA* | 170 Pa | 103 Pa | 10 min | −39% |

*0.23 mmol $H_2O_2$ + 5 mol % (0.011 mmol) AA

It is seen from Table 5 that a solution of 0.23 mmol $H_2O_2$+5 mol % AA is capable of rapidly degrading a broad range of polysaccharide-containing fillers, including HA-based, CMC-based, and alginate-based fillers. Within 10 minutes, 79% of the highly crosslinked HA gel was degraded. The other HA and CMC containing gels (i.e., Belotero® Intense, Glytone 4 Original, the CMC gel and Radiesse®) were degraded within 10 min to well below 10% of their initial mechanical strength. Notably, the calcium hydroxyapatite (CaHA) particles present in Radiesse® were found to not hinder the remarkable fast degradation of the carboxymethyl cellulose (CMC) polymers of Radiesse®.

The alginate-based gel (i.e. Novabel®) takes slightly longer to be degraded compared to the other polysaccharide gels studied. This is believed to be due to the fact that the alginate is present in the form of special three-dimensional gel spheres or is inherently less sensitive to degradation by free radicals.

In addition, as can also be seen from Table 5, the solution of 0.23 mmol $H_2O_2$+5 mol % AA is also able to degrade (poly)peptide-based gels, as exemplified by the gelatine gel. Within 10 min, the gelatine gel was degraded to 39% of its original mechanical strength. This demonstrates that the filler-degrading composition of the present invention is not limited to the degradation of polysaccharide-containing filler but may also be used for the degradation of (poly) peptide-based fillers.

Example 6

Degradation Capacity of a Mixture of $H_2O_2$ and AA in Comparison to Hyaluronidase In order to study the degradation capacity of $H_2O_2$+AA according to the present invention in comparison to the enzyme hyaluronidase, which is used in the prior art to enzymatically decompose HA fillers, 1000 µl of a crosslinked HA gel at 20 mg/ml made from the crosslinked HA matrix used in the manufacturing of Glytone 4 (Merz Aesthetics) was subjected to degradation by 0.06 mmol $H_2O_2$+0.01 mmol AA or 0.06 mmol $H_2O_2$+0.02 mmol AA in the same manner as described above for, e.g., the degradation study using 0.23 mmol $H_2O_2$+5 mol % (0.011 mmol) AA (cf. Example 1). As a comparison, the same gel was mixed with 40 U hyaluronidase. The decrease in storage modulus G' was measured over time. The results are shown in FIG. 2.

Figure 2:
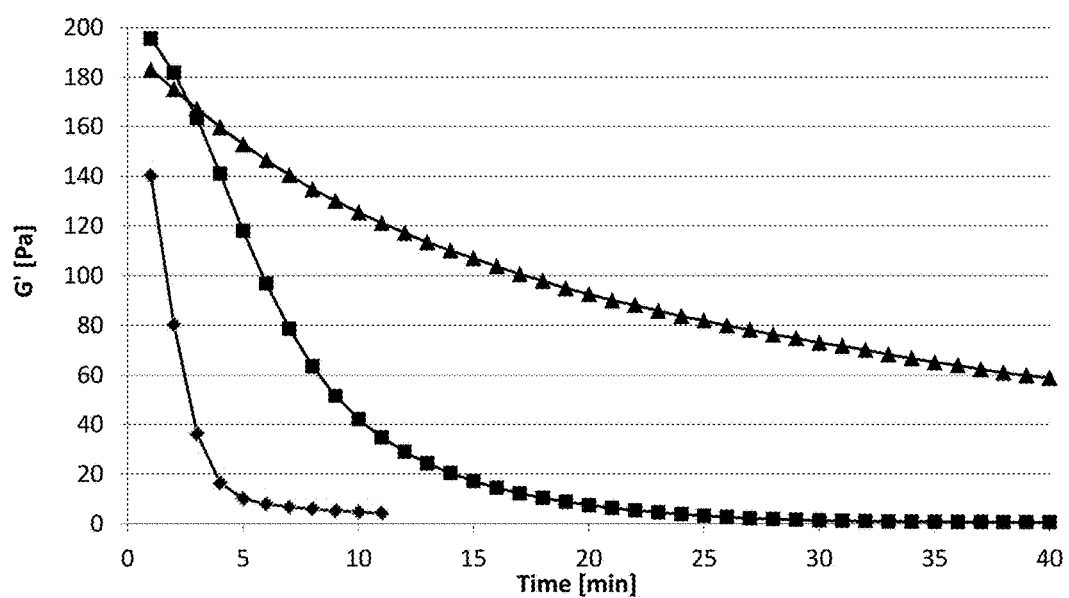
FIG. 2 illustrates the degradation capacity of a mixture of $H_2O_2$ and ascorbic acid (AA) in comparison to hyaluronidase. The decrease in storage modulus G' over time is shown for a crosslinked HA gel at 20 mg/ml made from the crosslinked HA matrix used in the manufacturing of Glytone 4 (Merz Aesthetics) for 40 U hyaluronidase (▲), 0.06 mmol $H_2O_2$+0.01 mmol ascorbic acid (AA) (■), and 0.06 mmol $H_2O_2$+0.02 mmol AA (♦).

As is seen from FIG. 2, the combination of $H_2O_2$ and AA results in a concentration-dependent, fast and, after a relatively short period of time, complete degradation of the HA gel. In contrast, the hyaluronidase treatment results in a slow degradation and reaches the half maximal G' value only after 20 min. Further, the hyaluronidase continues to be active and to enzymatically degrade the HA gel even at prolonged incubation times. In contrast, the $H_2O_2$+AA solution shows a "window of activity", which means that the HA gel is rapidly degraded in a defined and relatively short time frame. Hence, unlike hyaluronidase which continues to be active for a long period of time, the degradation induced by the combination of $H_2O_2$ and AA stops over time and, thus, enables full degradation control.

Example 7

Impact of the Added Amount of a $H_2O_2$ and AA Solution on the Extent of HA Gel Degradation In order to study the impact of the amount of $H_2O_2$ and AA on the degradation of a HA gel, 20 µl, 50 µl and 500 µl of a mixed solution of 0.06 mmol $H_2O_2$+0.04 mmol AA were added to and mixed with 1000 µl of a crosslinked HA gel at 26 mg/ml made from the crosslinked HA matrix used in the manufacturing of Glytone 4 (Merz Aesthetics) in the same manner as described above for, e.g., the degradation study using 0.23 mmol $H_2O_2$+5 mol % (0.011 mmol) AA (cf. Example 1). The decrease in storage modulus G' was measured over time. The results are shown in FIG. 3.

Figure 3:
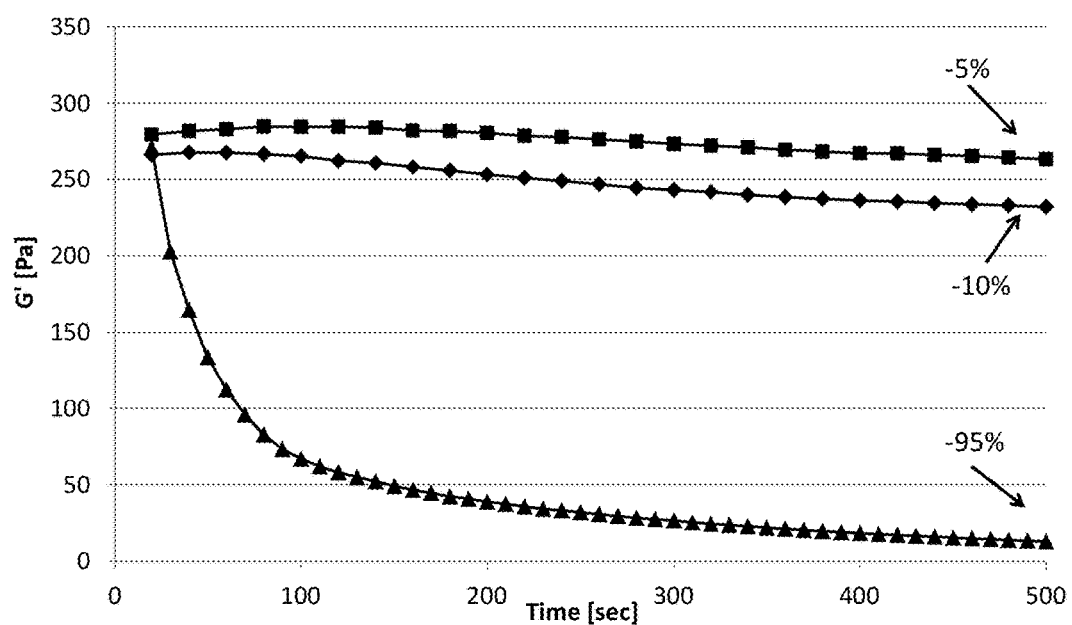
FIG. 3 illustrates the impact of the amount of a $H_2O_2$+ascorbic acid (AA) solution on the extent of degradation of a HA gel. The decrease in storage modulus G' over time is shown for a crosslinked HA gel at 26 mg/ml made from the crosslinked HA matrix used in the manufacturing of Glytone 4 (Merz Aesthetics) for the addition of 20 μl (■), 50 μl (♦), and 500 μl (▲) of a 0.06 mmol $H_2O_2$+0.04 mmol AA solution.

As can be seen from FIG. 3, dependent on the amount of $H_2O_2$ and AA added to the crosslinked HA gel, 5% to 95% of the original gel strength can be decomposed within a period of 500 seconds. Thus, the amount of added $H_2O_2$ and AA allows one to achieve a precise correction (reduction) of about 5% to 10% of the filler strength (see FIG. 3; addition of 20 µl and 50 µl $H_2O_2$+AA solutions: curves marked by black squares and rhombuses, respectively). On the other hand, if required or desired, essentially full degradation (about 95%) of the crosslinked HA gel can be achieved (see FIG. 3; 500 µl: curve marked by black triangles). In other words, depending on the amount of $H_2O_2$ and AA, degradation can be adjusted.

Example 8

Stepwise Degradation of a Crosslinked HA Gel by $H_2O_2$ and AA

This example shows that it is possible to control degradation of a crosslinked HA gel by the stepwise addition of a first $H_2O_2$+AA solution and subsequently a second $H_2O_2$+AA solution. First, 500 µl of a solution of 0.06 mmol $H_2O_2$+0.01 mmol AA were added to 1000 µl of a crosslinked HA gel at 34 mg/ml made from the crosslinked HA matrix used in the manufacturing of Glytone 4 (Merz Aesthetics). After about 170 seconds, the degradation effect of the first solution declined, and 500 µl of a solution of 0.06 mmol $H_2O_2$+0.01 mM AA were then added to the (partially degraded) HA gel. The results are shown in FIG. 4.

Figure 4:
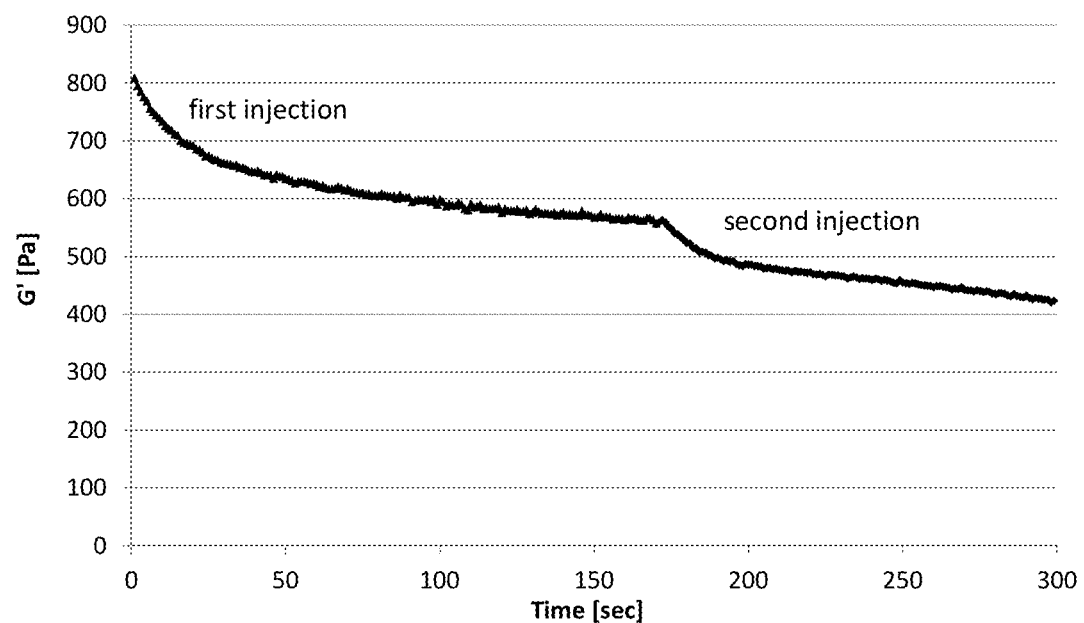
FIG. 4 illustrates the degradation of a HA filler in a stepwise manner. The decrease in storage modulus G' over time is shown for a first addition of 50 μl of a $H_2O_2$+AA solution (0.06 mmol $H_2O_2$+0.01 mmol AA), followed by (after about 170 seconds) a second addition of 50 μl of a $H_2O_2$+AA solution (0.06 mmol $H_2O_2$+0.01 mmol AA) to a crosslinked HA gel at 34 mg/ml made from the crosslinked HA matrix used in the manufacturing of Glytone 4 (Merz Aesthetics).

As is apparent from FIG. 4, the HA gel can be degraded in a stepwise fashion which thus provides another possibility to control or adjust degradation. In addition, the results demonstrate that generation of free oxygen radicals is limited over time.

In summary, the above results show that a combination of a source of oxygen radicals (e.g., $H_2O_2$) and a booster of oxygen free radical generation (e.g., ascorbic acid) allows for a faster degradation than the conventionally used hyaluronidase enzyme, resulting in an immediate correction effect. Furthermore, it enables the degradation of all polysaccharide-containing fillers, not only HA fillers.

In addition, the composition of the present invention allows partial as well as full degradation of unwanted fillers. Also, the rate and extent of the degradation can be readily controlled and individually adapted to the specific case. Moreover, since the chemical pathway mimics native digestion in tissue, the composition of the present invention is expected to be well tolerated.

The invention claimed is:

1. A method for in vivo treatment of unwanted polysaccharide-containing filler depots or of polysaccharide-containing filler misplacements, asymmetries or overcorrections, comprising administering to a subject a pharmaceutical composition into said filler depots or filler misplacements, asymmetries or overcorrections or in close proximity of said filler depots or filler misplacements, asymmetries or overcorrections, wherein the pharmaceutical composition comprises:
    (a) at least one source of oxygen free radicals selected from hydrogen peroxide and adducts thereof, and
    (b) at least one catalyst of oxygen free radical generation from said at least one source of oxygen free radicals selected from ascorbic acid, salts thereof and derivatives thereof, and
    wherein said at least one source of oxygen free radicals is present in the composition in a concentration of from 29 mM to 1.45 M, and said at least one catalyst of oxygen free radical generation from said at least one source of oxygen free radicals is present in the composition in a concentration of from 57 mM to 0.57 M;
    wherein the pharmaceutical composition degrades a crosslinked hyaluronic acid gel within less than 20 minutes after mixing 40 μL of the pharmaceutical composition in the form of an aqueous solution with 1000 mg of the crosslinked hyaluronic acid gel, wherein said degradation is indicated by a decline in the storage modulus (G') of more than 90% of the start value of the mixture of said aqueous solution and said crosslinked hyaluronic acid gel; and
    wherein the filler is a crosslinked hyaluronic acid-based filler.

2. The method of claim 1, wherein said at least one catalyst of oxygen free radical generation from said at least one source of oxygen free radicals is present in the composition in a concentration of from 0.085 M to 0.17 M.

3. The method of claim 1, wherein said administering comprises injecting the pharmaceutical composition into the subject.

4. The method of claim 1, wherein the composition further comprises a pharmaceutically acceptable carrier.

5. The method of claim 4, wherein the pharmaceutically acceptable carrier comprises phosphate buffered saline.

6. The method of claim 1, wherein the composition further comprises an anesthetic agent.

7. The method of claim 6, wherein the anesthetic agent is lidocaine.

8. The method of claim 1, comprising administering to the subject the pharmaceutical composition into said filler depots or filler misplacements, asymmetries or overcorrections.

9. The method of claim 1, comprising administering to the subject the pharmaceutical composition in close proximity of said filler depots or filler misplacements, asymmetries or overcorrections.

10. The method of claim 1, wherein said administering comprises injecting the composition into the subject subcutaneously.

11. The method of claim 1, wherein said administering comprises injecting the composition into the subject intradermally.

12. The method of claim 1, wherein the composition further comprises one or more substances selected from the group consisting of buffers, osmolarity adjusting agents, antioxidants, salts, chelating agents, peptides, proteins, polysaccharides, and pharmaceutically active ingredients.

13. The method of claim 1, wherein the at least one source of oxygen free radicals is hydrogen peroxide.

14. The method of claim 1, wherein the at least one catalyst of oxygen free radical generation is ascorbic acid.

15. The method of claim 1, wherein said at least one source of oxygen free radicals is present in the composition in a concentration of from 0.29 M to 0.88 M.

16. The method of claim 1, wherein said at least one catalyst of oxygen free radical generation from said at least one source of oxygen free radicals is present in the composition in a concentration of from 0.085 M to 0.17 M.

17. The method of claim 1, wherein the molar ratio of the oxygen free radical source to the catalyst is 50:1 to 10:1.

* * * * *